United States Patent [19]

Scherzer et al.

[11] Patent Number: 5,207,942
[45] Date of Patent: May 4, 1993

[54] PREPARATION OF MIXTURES OF DIPHENYLMETHANE DIISOCYANATES AND POLYPHENYLPOLYMETHYLENE POLYISOCYANATES HAVING A REDUCED IODINE COLOR NUMBER

[75] Inventors: Dietrich Scherzer, Ludwigshafen; Roland Minges, Gruenstadt; Werner Langer; Bernd Bruchmann, both of Ludwigshafen; Wolfgang Heider, Limburgerhof; Peter Keller, Hirschberg; Arnold Schmitt, Friedelsheim; Willy Van Pee, Kapellen, all of Fed. Rep. of Germany

[73] Assignee: BASF Aktiengesellschaft, Fed. Rep. of Germany

[21] Appl. No.: 653,566

[22] Filed: Feb. 8, 1991

[30] Foreign Application Priority Data

Mar. 6, 1990 [DE] Fed. Rep. of Germany ....... 4006976

[51] Int. Cl.$^5$ .................... C09K 3/00; C07C 263/10
[52] U.S. Cl. .................... 252/182.2; 560/347
[58] Field of Search ........... 252/182.2, 182.21, 182.22; 560/347

[56] References Cited

U.S. PATENT DOCUMENTS

| T881,001 | 12/1970 | Werts et al. | 252/182 |
|---|---|---|---|
| 2,957,903 | 10/1960 | Spiegler | 260/453 |
| 3,359,295 | 12/1967 | Shultz et al. | 260/453 |
| 3,488,374 | 1/1970 | Kober et al. | 260/453 |
| 3,644,457 | 2/1972 | König et al. | 260/453 |
| 3,715,381 | 2/1973 | Spannburgh et al. | 260/453 P |
| 3,723,363 | 3/1973 | Shaw | 252/182 |
| 3,914,269 | 10/1975 | Narsasian | 560/347 |
| 4,014,914 | 3/1977 | Pistor et al. | 560/347 |
| 4,118,411 | 10/1978 | Reiff et al. | 260/453 SP |
| 4,297,472 | 10/1981 | Heiss | 528/84 |
| 4,405,527 | 9/1983 | Wegener et al. | 560/347 |
| 4,518,761 | 5/1985 | Richter et al. | 528/67 |
| 4,552,902 | 11/1985 | Nafziger et al. | 252/182 |
| 4,677,154 | 6/1987 | Narayan et al. | 252/182 |
| 4,743,627 | 5/1988 | Narayan et al. | 252/182.21 |
| 4,800,040 | 1/1989 | Hostettler | 252/182.22 |
| 4,814,103 | 3/1989 | Potter et al. | 252/182.22 |
| 4,972,004 | 11/1990 | Randall et al. | 252/182.22 |
| 4,986,929 | 1/1991 | Williams | 252/182.22 |
| 5,028,636 | 7/1991 | Gebauer et al. | 252/182.22 |
| 5,144,031 | 9/1992 | Pedar | 252/182.2 |

OTHER PUBLICATIONS

Derek Williams *Chemical Abstracts*, vol. 64, abstract #64:6559a, of G.B. 1,014,043.

*Primary Examiner*—Edward A. Miller
*Attorney, Agent, or Firm*—Martin P. Connaughton

[57] ABSTRACT

Mixtures of diphenylmethane diisocyanates and polyphenylpolymethylene polyisocyanates (crude MDI) having a reduced iodine color number are prepared by reacting the corresponding mixtures of diphenylmethanediamines and polyphenylpolymethylene-polyamines with phosgene in the presence of one or more inert organic solvents at elevated temperatures by a process in which low molecular weight alkanols, polyhydric alcohols, preferably dihydric to octahydric alcohols having a molecular weight of from 60 to 350, or mixtures thereof are incorporated in an effective amount, advantageously in an amount of from 0.01 to 5% by weight, based on the weight of crude MDI, into the reaction mixture after the end of the phosgenation, the phosgene and the inert organic solvent are then separated off, from 0 to 5% by weight, based on the weight of crude MDI, of one or more phenol-based antioxidants and/or aryl phosphite are added to the reaction product, and the reaction mixture is subjected to a thermal treatment.

9 Claims, No Drawings

PREPARATION OF MIXTURES OF DIPHENYLMETHANE DIISOCYANATES AND POLYPHENYLPOLYMETHYLENE POLYISOCYANATES HAVING A REDUCED IODINE COLOR NUMBER

BACKGROUND OF THE INVENTION

1. Field of the Invention

The present invention relates to a process for the preparation of mixtures of diphenylmethane diisocyanates and polyphenylpolymethylene polyisocyanates, i.e. crude MDI, having a reduced iodine color number by reacting the corresponding mixture of a diphenylmethanediamine and a polyphenylpolymethylenepolyamine, i.e. crude MDA, with phosgene in the presence of one or more inert organic solvents, wherein a low molecular weight alkanol or a polyhydric alcohol or a mixture thereof is incorporated, in an effective amount, into the reaction mixture after the end of the phosgenation.

2. Description of Related Art

Crude MDI, one of the industrially most important starting materials for the production of polyisocyanate polyadducts, for example foams containing urethane groups or urethane and isocyanurate groups, and of diphenylmethane 4,4'-diisocyanate, an important component for the production of polyurethane (PU) elastomers, fibers, sealing compounds, adhesives, etc., is known to be prepared by phosgenating crude MDA, usually in the presence of an inert organic solvent. Crude MDA in turn is obtained by condensation of aniline and formaldehyde in the presence of acidic catalysts, and the percentage of diphenylmethanediamines and of the homologous polyphenylpolymethylenepolyamines and their isomers can be controlled as a function of the selected ratios of the starting materials and the reaction conditions and the various methods (Kunststoff-Handbuch, Volume 7, Polyurethane, 1st edition 1966 and 2nd edition 1983, Carl-Hanser-Verlag, Munich, Vienna). If the condensation of aniline and formaldehyde is carried out, for example, in the presence of weakly acidic catalysts, crude MDA mixtures having a relatively high content of 2,2'-and 2,4'-diaminodiphenylmethanes are obtained, while crude MDA mixtures having a high content of 4,4'-diaminodiphenylmethane and at the same time a low content of 2,4'-diaminodiphenylmethane can be prepared only in the presence of relatively large amounts of strongly acidic catalysts, preferably of strong mineral acids, e.g. hydrochloric acid.

The ratio of diaminodiphenylmethane isomers to the higher homologs in the crude MDA is furthermore dependent on the aniline/formaldehyde ratio and on the condensation temperature, higher aniline/formaldehyde ratios and low condensation temperatures resulting in high diaminodiphenylmethane contents (CA-A-700 026).

The disadvantage of these preparation processes, which are described in many publications in the literature and in many patents, is the formation of more or less strongly colored crude MDA, whose color may vary from black through darker and paler brown hues to ochre. Another disadvantage is that these discolorations are reduced insufficiently, if at all by the subsequent phosgenation for the preparation of the corresponding crude MDI, and the crude MDI formed cannot be purified by distillation. This undesirable discoloration is further-more effective in the secondary products, so that even the noncellular or cellular polyisocyanate polyadducts produced from colored crude MDI are not colorless. Although the intrinsic color of the polyisocyanate polyadducts does not have an adverse effect on their mechanical properties, the consumer wants essentially colorless products.

There has therefore been no lack of attempts to reduce the discoloration of crude MDI and to stabilize the prepared polyisocyanates by suitable process measures or additives.

According to U.S. Pat. No. 2 885 420, organic polyisocyanates can be stabilized to discoloration by the addition of from 0.01 to 0.5% by weight, based on the weight of polyisocyanate, of an aromatic, cycloaliphatic or aliphatic ether or thioether.

To eliminate impurities in organic diisocyanate solutions, which impurities act as gelling catalysts, according to DE-A-1 280 855 (GB 1 097 219) about 0.001-1% by weight, based on the weight of the diisocyanate, of phosphoric acid is added to said solutions.

GB-B-1 465 014 describes the addition of glycidol in an amount of from 0.001 to 0.25% by weight, based on the weight of diisocyanate, for improving the shelf life of distilled diphenylmethane diisocyanates.

EP-B-0 183 976 (U.S. Pat. No. 4,677,221) relates to a process for the preparation of (cyclo)aliphatic diisocyanates having high-temperature color stability, wherein a technical-grade diisocyanate having aliphatically and-/or cycloaliphatically bonded isocyanate groups is heated in the presence of from 0.1 to 3% by weight of a compound which is soluble in the diisocyanate and has not less than 3% by weight of structural units of the formula —NH—CO— for not more than 5 hours at from 100° to 220° C., and the diisocyanate treated in this manner is then purified by distillation. The process is not applicable to the treatment of crude MDI, since, as stated above, the latter cannot be distilled.

According to U.S. Pat. No. 4,465,639, from 0.1 to 5% by weight, based on the weight of polyisocyanate in the reaction mixture, of water are incorporated into crude MDI after the end of phosgenation but before the phosgene has been completely separated off. This measure makes it possible to lighten the color of the crude MDI and of the PU foams produced therefrom. Furthermore, the proportion of relatively high molecular weight MDI homologs in the crude MDI is substantially decreased and their viscosity reduced. Although this makes it possible to reduce the iodine color number of the crude MDI, this method also has considerable disadvantages. As a result of the presence of water, the corrosive effect of the reaction mixture containing chlorine, hydrogen chloride and phosgene on the apparatuses of the production plant is substantially increased and therefore the risk of leakage, associated with the escape of toxic phosgene or of a phosgene-containing reaction mixture, is increased. For safety reasons, moisture in any form is therefore advantageously essentially completely excluded during phosgenation.

DETAILED DESCRIPTION OF THE INVENTION

It is an object of the present invention to match the iodine color number of crude MDI to a level achievable by the addition of water or to reduce it even further, while avoiding the stated disadvantages, it being intended in particular to dispense with the addition of water.

We have found that this object is achieved, surprisingly, by the addition of monohydric and/or polyhydric alcohols to the phosgene-containing reaction mixture after the end of the phosgenation.

The present invention therefore relates to a process for the preparation of crude MDI having a reduced iodine color number by reacting the crude MDA with phosgene in the presence of one or more inert organic solvents at elevated temperatures, separating off the excess phosgene and solvent after the end of the phosgenation and subjecting the resulting reaction product to a thermal treatment, wherein a low molecular weight alkanol or, preferably, a polyhydric alcohol or a mixture of a low molecular weight alkanol and polyhydric alcohol is incorporated in an effective amount into the reaction mixture after the end of the phosgenation.

As a result of the addition, according to the invention, of the monohydric and/or polyhydric alcohols, the iodine color number of crude MDI can be substantially reduced, for example to less than 60, preferably from 40 to 6 or less, in particular from 20 to 6 or less.

The mixtures, prepared by the novel process, of diphenylmethane diisocyanates (MDI) and polyphenylpolymethylene polyisocyanates furthermore advantageously have an MDI isomer content of from 30 to 90, preferably from 30 to 70, % by weight, and NCO content of 31±2, preferably 31±1.0, % by weight, based in each case on the weight of crude MDI, and a viscosity of not more than 2,000, preferably from 50 to 500, mPa.s, measured at 23° C.

As stated above, crude MDI having such isomer and homolog compositions can be prepared by phosgenating crude MDA having corresponding compositions in the presence of one or more inert organic solvents by known methods.

Suitable crude MDAs are advantageously obtained by condensing aniline and formaldehyde in a molar ratio of from 6:1 to 1.6:1, preferably from 3:1 to 2:1, and in a molar ratio of aniline to acidic catalyst of from 1:0.98 to 1:0.01, preferably from 1:0.8 to 1:0.2.

The formaldehyde is preferably used in the form of an aqueous solution, for example as commercial 30–40% strength by weight solution.

Proton donors, for example acidic ion exchange resins or strong organic and, preferably, inorganic acids, have proven useful as acidic catalysts. Strong acids in this case are those having a pKa of less than 1.5; in the case of polybasic acids, this value applies to the first hydrogen dissociation. Examples are hydrochloric acid, sulfuric acid, phosphoric acid, fluorosulfonic acid and oxalic acid. Hydrogen chloride can also be used in the form of a gas. Aqueous hydrochloric acid in concentrations of about 25–31% by weight is preferably used.

Suitable processes for the preparation of crude MDA are described in, for example, CA-A-700 026, DE-B-22 27 110 (U.S. Pat. No. 4,025,557), DE-B-22 38 920 (U.S. Pat. No. 3,996,283), DE-B-24 26 116 (GB-A-1 450 632), DE-A-12 42 623 (U.S. Pat. No. 3,478,099), GB-A-1 064 559 and DE-A-32 25 125.

Phosgene is used as the other starting component for the preparation of crude MDI. The gaseous phosgene can be used as such or can be diluted with gases which are inert under the reaction conditions, such as nitrogen, carbon monoxide, etc. The molar ratio of crude MDA to phosgene is advantageously such that there are from 1 to 10, preferably from 1.3 to 4, moles of phosgene in the reaction mixture per $NH_2$ group.

Suitable inert organic solvents are compounds in which the crude MDA and the phosgene are partially or completely soluble.

Solvents which have proven excellent are chlorinated, aromatic hydrocarbons, e.g. 0-diohlorobenzene, p-dichlorobenzene, trichlorobenzenes, the corresponding toluenes and xylenes, chloroethylbenzene, monochlorodiphenyl, α- and β-naphthyl chloride and in particular chlorobenzene and dialkyl phthalates, such as diethyl phthalate. The solvents can be used individually or as mixtures. An advantageously used solvent is one which has a boiling point which is lower than that of the MDI isomers, so that the solvent can readily separated off from the crude MDI by distillation. The amount of solvent is advantageously such that the reaction mixture has an isocyanate content of from 2 to 40, preferably from 5 to 20, % by weight, based on the total weight of the reaction mixture.

The crude MDA can be used as such or in solution in organic solvents. In particular, however, crude MDA solutions having an amine content of from 2 to 40, preferably from 5 to 20, % by weight, based on the total weight of the amine solution, are used.

To reduce the iodine color number, according to the invention, a low molecular weight alkanol or, preferably, a polyhydric alcohol or a mixture of a low molecular weight alkanol and a polyhydric alcohol is incorporated into the phosgene-containing reaction mixture. Other suitable polyhydric alcohols are starches, such as wheat starch, corn starch, rice starch or potato starch, and sugar derivatives.

Low molecular alkanols which can be used according to the invention are secondary, tertiary and, preferably, primary alkanols having branched or, preferably, straight-chain alkyl radicals of to 10, preferably 1 to 4, carbon atoms. Examples are methanol, ethanol, n-propanol, isopropanol, n-butanol, sec-butanol, tert-butanol, pentanol, hexanol and n- and isooctanols.

Suitable polyhydric alcohols are advantageously dihydric to octahydric, preferably dihydric or trihydric and, except for the relatively high molecular weight starches, advantageously have a molecular weight of from 60 to 350, preferably from 60 to 150. Examples of suitable polyhydric alcohols are alkanediols, advantageously those of 2 to 8, preferably 2 to 6, carbon atoms, e.g. propane-1,3-diol, 2,2-dimethylpropane-1,3-diol, butane-1,4-diol, 2-methyl- and 2,2-dimethylbutane-1,4-diol, pentane-1,5-diol, 2-ethylpentanedio, hexane-1,6-diol and, preferably, ethanediol, trihydric alcohols, advantageously those of 3 to 9 carbon atoms, e.g. trimethylolpropane, triethanolpropane, hexanetriols, trihydroxycyclohexane, and, preferably, glycerols, and alcohols which are tetrahydric or contain a large number or hydroxyl groups and are advantageously of from 4 to 12 carbon atoms, e.g. hexanetetrols, pentaerythritol, sorbitol, inositol and sucrose. Among the monohydric and polyhydric alcohols, glycerol has proven particularly useful, so that this trihydric, industrially readily available alcohol is used in particular.

The low molecular weight alkanols and/or polyhydric alcohols can be used in pure or technical-grade products should be very low, advantageously less than 0.1% by weight. Mixtures of alkanols or polyhydric alcohols or mixtures of one or more alkanols and one or more polyhydric alcohols can also be used.

The alkanols and/or polyhydric alcohols which can be used according to the invention are advantageously employed in an amount of from 0.01 to 5, preferably from 0.2 to 1.6, in particular from 0.4 to 0.8, % by weight, based on the weight of the solvent-free crude MDI.

After the excess phosgene and the inert solvent are separated off, a phenol-based antioxidant, one or more aryl phosphites or a mixture of these stabilizers can, if required, be added to the crude MDI containing low molecular weight alkanols and polyhydric alcohols and/or reaction products obtainable from these monohydric and/or polyhydric alcohols and crude MDI. If these stabilizers, which in conjunction with the low molecular weight alkanols and/or polyhydric alcohols used according to the invention additionally reduce the iodine color number, are used, they are advantageously employed in an amount of from 0 to not more than 5, preferably from 0.01 to 3, in particular from 0.1 to 1.0, % by weight, based on the weight of the crude MDI.

Examples of suitable phenol-based antioxidants are styrene-substituted phenols, i.e. phenols which contain a bound 1-phenylethyl group in the 2- or 4-position or in the 2- and 4-and/or 6-position, bis-[2-hydroxy-5-methyl-3-tert-butylphenyl]methane, 2,2-bis-[4-hydroxyphenyl]-propane, 4,4'-dihydroxybiphenyl, 3,3'-dialkyl- or 3,3',5,5'-tetraalkyl-4,4'-dihydroxybiphenyl, bis-[4-hydroxy-2-methyl-5-tert-butylphenyl]sulfide, hydroquinone, 4-methoxy-, 4-tert-butoxy- or 4-benzyloxyphenol, mixtures of 4-methoxy-2- and -3-tert-butylphenol, 2,5-dihydroxy-1-tert-butylbenzene, 2,5-dihydroxy-1,4-di-tert-butylbenzene, 4-methoxy-2,6-di-tert-butylphenol and, preferably, 2,6-di-tert-butyl-p-cresol.

Aryl phosphites which have proven useful are tri-(alkylphenyl) phosphites where alkyl is of 1 to 10 carbon atoms, e.g. tri-(methylphenyl), tri-(ethylphenyl), tri-(n-propylphenyl), tri-(isopropylphenyl), tri-(n-butylphenyl), tri-(sec-butylphenyl), tri-(tert-butylphenyl),tri-(pentylphenyl),tri-(hexylphenyl), tri-(2-ethylhexylphenyl), tri-(octylphenyl), tri-(2-ethyloctylphenyl) and tri-(decylphenyl) phosphite and preferably tri-(nonylphenyl) phosphite and in particular triphenyl phosphite.

For the preparation of the crude MDIs having a reduced iodine color number by the novel process, the corresponding crude MDAs are advantageously phosgenated at from 90° to 220° C., preferably from 120° to 180° C., under superatmospheric pressure, for example from 1 to 10, preferably from 1 to 3, bar, or, in particular, under atmospheric pressure. The temperature used in the novel process is above the decomposition temperature of the carbamoyl chlorides formed as intermediates by the reaction of crude MDA with phosgene. Increasing the pressure is subject only to technical and possibly safety limits, although the yield is not increased any further by a greater increase in pressure.

After the end of the phosgenation, the low molecular weight alkanol and/or the polyhydric alcohol, in particular glycerol, is or are incorporated into the reaction mixture, which consists of one or more inert organic solvents, dissolved crude MDI, excess phosgene, hydrogen chloride and byproducts of the phosgenation, at from 20° to 150° C., preferably from 70° to 120° C., in particular from 80° to 110° C. After a residence time of from 0.01 to 45, preferably from 2 to 25, minutes at from 20° to 150° C., preferably from 70° to 120° C., the excess phosgene is essentially completely separated off, preferably by distillation, under atmospheric pressure, after which the inert organic solvent or a mixture of such solvents is essentially completely separated off, preferably by distillation, at from 30° to 180° C., preferably from 50° to 150° C., under reduced pressure, for example from 0.01 to 100, preferably from 0.1 to 50, mbar.

If appropriate, one or more phenol-based antioxidants and/or one or more aryl phosphites can be added, in an effective amount, to the crude MDI's containing low molecular weight alkanols and/or polyhydric alcohols and/or reaction products of these alcohols with crude MDI. For dechlorination, the crude MDIs treated in this manner are then heated to 100°-250° C., preferably 140°-200° C., and are treated at this temperature under a pressure of from 0.01 to 100, preferably from 0.1 to 20, mbar for not less than 5, in particular from 5 to 45, minutes. After cooling to 60° C., the crude MDI is placed in temporary storage, where it is left to cool further.

The crude MDIs prepared by the novel process have a substantially reduced iodine color number, usually not more than 60, and are used for the production of compact or expanded polyisocyanate polyadducts, preferably flexible, semirigid or rigid foams which contain urethane groups or urethane and isocyanurate groups and have a substantially paler color.

EXAMPLES 1 TO 13 AND COMPARATIVE EXAMPLES I AND V

The alkanols or polyhydric alcohols or the comparative substances were added, at 105° C., to a reaction mixture which consisted of, per 100 parts by weight, 80 parts by weight of monochlorobenzene as a solvent, 10 parts by weight of excess phosgene and 10 parts by weight of crude MDI, which in turn contained 50% by weight of 4,4'-MDI,
4% by weight of 2,4'-MDI,
0.04% by weight of 2,2'-MDI and
45.96% by weight of homologs having more than two isocyanate groups, the percentages being based on the weight of crude MDI.

The reaction mixture was then heated to 140° C. in about 20 minutes and the excess phosgene was distilled off under atmospheric pressure in the course of 20 minutes with the aid of a rotary evaporator.

The reaction mixture was then left to cool to 100°-120° C. in about 10 minutes, and the monochlorobenzene was essentially completely distilled off in this temperature range under reduced pressure (from 50 to 10 mbar) in the course of about 15 minutes.

If required, the phenol-based antioxidants and the aryl phosphite were then incorporated into the crude MDI containing an alkanol and/or polyhydric alcohols and/or reaction products of these alcohols with crude MDI, after which the crude MDI containing the alkanol and/or polyhydric alcohols and/or reaction products of these alcohols with crude MDI and, where relevant, the stabilizers was dechlorinated at 180° C. or 210° C. and 10 mbar for 30 minutes.

The alkanols and polyhydric alcohols used and the comparative substances and any stabilizers and the amounts thereof and the iodine color numbers measured for the crude MDIs obtained are summarized in the Table below.

TABLE

| | Type | Amount [%]* | Type | Amount [%]* | Iodine Color Number After Dechlorination at 180° C. or 210° C. | |
|---|---|---|---|---|---|---|
| Comparative Examples | Addition After End of Phosgenation | | Addition After Solvent has Been Distilled Off | | | |
| I   Crude MDI | — | — | — | — | 100 | 100 |
| II  Crude MDI | Water | 1.0 | — | — | 12 | 15 |
| III Crude MDI | Water | 0.5 | — | — | 20 | 30 |
| IV  Crude MDI | Water | 0.1 | — | — | 20 | 30 |
| V   Crude MDI | Water | 0.02 | — | — | 30 | 35 |
| Examples | Alkanols or polyhydric alcohols | | Stabilizer | | | |
| 1   Crude MDI | Methanol | 0.5 | — | — | 40 | 60 |
| 2   Crude MDI | Butanol | 0.5 | — | — | 50 | 60 |
| 3   Crude MDI | Ethylene glycol | 0.02 | — | — | 30 | 40 |
| 4   Crude MDI | Ethylene glycol | 0.5 | — | — | 20 | 35 |
| 5   Crude MDI | Ethylene glycol | 0.5 | Di-tert-butyl-cresol | 0.5 | 18 | 35 |
| 6   Crude MDI | Ethylene glycol | 0.5 | Triphenyl phosphite | 0.5 | 18 | 15 |
| 7   Crude MDI | Glycerol | 0.1 | — | — | 30 | 35 |
| 8   Crude MDI | Glycerol | 0.4 | — | — | 12 | 20 |
| 9   Crude MDI | Glycerol | 0.7 | — | — | 9 | 20 |
| 10  Crude MDI | Glycerol | 1.0 | — | — | 7 | 18 |
| 11  Crude MDI | Glycerol | 1.5 | — | — | 6 | 18 |
| 12  Crude MDI | Glycerol | 0.5 | Di-tert-butyl cresol | 0.5 | 8 | 18 |
| 13  Crude MDI | Glycerol | 0.5 | Triphenyl phosphite | 0.5 | 8 | 20 |

*Based on crude MDI

We claim:

1. A process for the preparation of a mixture of diphenylmethane diisocyanates and polyphenylpolymethylene polyisocyanates having a reduced iodine color number, by reacting:
   a) a corresponding mixture of a diphenylmethane diamines; with
   b) phosgene, in the presence of one or more inert solvents;
   c) adding, in an amount sufficient to reduce the iodine color, a low molecular weight alkanol and/or polyhydric alcohol at the end of the phosgenation but prior to separating off any excess phosgene and the insert solvent;
   d) separating off excess phosgene and unreacted solvent; and,
   e) dechlorinating the mixture of diphenylmethane diisocyanates and polyphenylpolymethylene polyisocyanates by heating under pressure.

2. A process as claimed in claim 1, wherein the low molecular weight alkanol, polyhydric alcohol or mixture thereof is incorporated into the reaction mixture in an amount of from 0.01 to 5% by weight, based on the weight of the mixture of diphenylmethane diisocyanates and polyphenylpolymethylene polyisocyanates.

3. A process as claimed in claim 1, wherein the polyhydric alcohol is dihydric to octahydric and has a molecular weight of from 60 to 350.

4. A process as claimed in claim 1, wherein the polyhydric alcohol is glycerol.

5. A process as claimed in claim 1, wherein the resulting mixture of diphenylmethane diisocyanates and polyphenylpolymethylene polyisocyanates has a diphenylmethane diisocyanate isomer content of from 30 to 90% by weight, an NCO content of $31 \pm 2\%$ by weight based in each case on the total weight, a viscosity of not more than 2,000 mPa.s at 23° C. and an iodine color number of not more than 60.

6. A process as claimed in claim 1 further incorporating one or more phenol-based antioxidants and/or one or more aryl phosphites in the mixture of diphenylmethane diisocyanates and polyphenyl-polymethylene polyisocyanates, containing low molecular weight alkanols and/or polyhydric alcohols, after the excess phosgene and the inert organic solvent have been separated off and before the reaction product is subjected to thermal treatment.

7. A process as claimed in claim 5, wherein one or more phenol-based antioxidants in an amount of not more than 5% by weight and/or one or more aryl phosphites in an amount of not more than 5% by weight, based in each case on the weight of the mixture of diphenylmethane diisocyanates and polyphenyl-polymethylene polyisocyanates, are incorporated into the mixture of diphenylmethane diisocyanates and polyphenylpolymethylene polyisocyanates, containing low molecular weight alkanols and/or polyhydric alcohols, after the excess phosgene and the inert organic solvent have been separated off and before the reaction product has been subjected to a thermal treatment.

8. A process as claimed in claim 6, wherein the phenol-based antioxidant consist of di-tert-butyl-p-cresol and the aryl phosphite consists of triphenyl phosphite.

9. A process as claimed in claim 1, wherein from 0.01 to 5% by weight, based on the weight of the mixture of diphenylmethane diisocyanates and polyphenylpolymethylene polyisocyanates in the reaction mixture, of glycerol is incorporated into the reaction mixture after the end of the phosgenation, after which the excess phosgene and the inert organic solvent are distilled off, subsequently from 0 to 5% by weight, based on the mixture of diphenylmethane diisocyanates and polyphenylpolymethylene polyisocyanates, of di-tert-butyl-p-cresol and/or triphenylphosphite are added to the reaction mixture, and the reaction product is then dechlorinated by heating under pressure.

* * * * *